United States Patent [19]

Stapleton

[11] Patent Number: 4,527,898
[45] Date of Patent: Jul. 9, 1985

[54] DISTINCTNESS OF IMAGE METER

[75] Inventor: Thomas T. Stapleton, Bloomfield Hills, Mich.

[73] Assignee: General Motors Corporation, Detroit, Mich.

[21] Appl. No.: 453,626

[22] Filed: Dec. 27, 1982

[51] Int. Cl.³ .................... G01N 21/55; G01N 21/57
[52] U.S. Cl. ................................ 356/446; 356/447; 356/125; 350/275
[58] Field of Search ............... 356/445, 446, 447, 448; 350/275, 273, 274

[56] References Cited

U.S. PATENT DOCUMENTS

| | | | |
|---|---|---|---|
| 2,720,812 | 10/1955 | Middleton | 356/447 |
| 2,975,285 | 3/1961 | Palmer | 356/445 |
| 3,551,041 | 12/1970 | McGivern | 350/275 |

OTHER PUBLICATIONS

Matsuta et al., "Development of a Gloss Tester for Paint Coatings", Japanese Journal of Applied Physics, vol. 21, No. 1, Jan. 1982, pp. 133-136.

Primary Examiner—R. A. Rosenberger
Assistant Examiner—Michael F. Vollero
Attorney, Agent, or Firm—Warren D. Hill

[57] ABSTRACT

In order to obtain an objective measurement of paint gloss on a flat or slightly curved surface, a distinctness of image instrument is provided having a light source for projecting a light beam onto the test surface, a detector responsive to reflected light from the surface, an aperture at the detector, a chopper near the light source and a lens for imaging the chopper blade on the plane of the aperture so that the sharpness of the image depends upon the reflective quality of the test surface. The rate of change of the detector output signal is large for a high glass surface while the rate of change is low for a low gloss surface. For use of the instrument on curved as well as flat surfaces the chopper is provided with a plurality of blades spaced at different distances from the light source. The blade image which is more nearly focussed on the aperture will produce a larger rate of change in the detector signal and the signal with the largest rate of change is chosen as the one representative of the surface quality.

2 Claims, 2 Drawing Figures

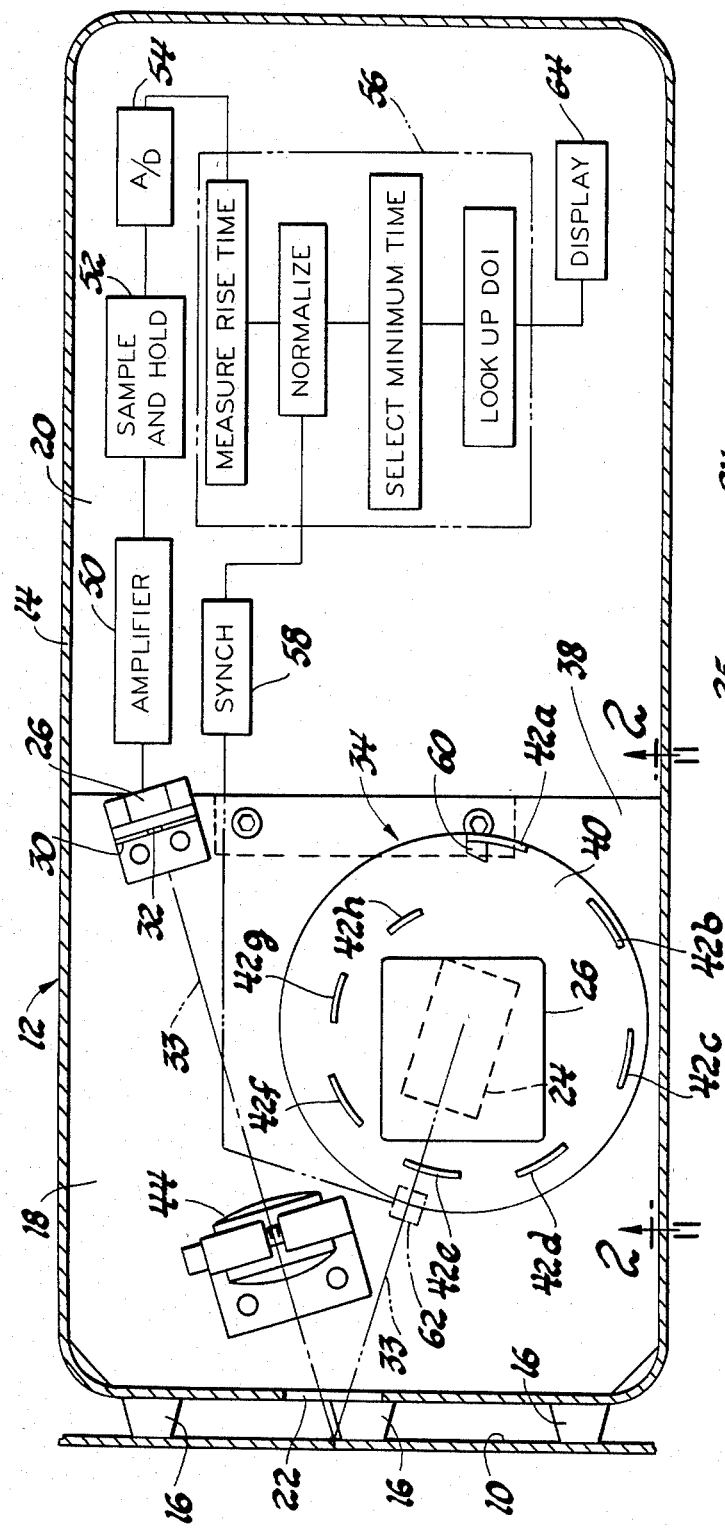
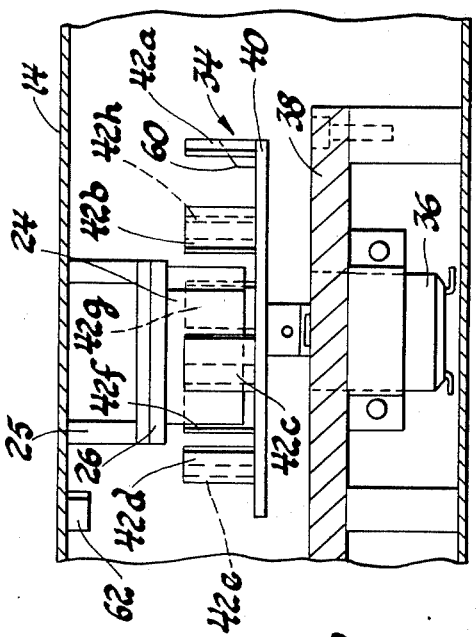
Fig. 1
Fig. 2

DISTINCTNESS OF IMAGE METER

This invention relates to a distinctness of image instrument for measuring the reflective quality of a surface.

It is desirable, for example, in inspecting the paint quality of an article of manufacture such as an automobile to have an instrument for measuring the paint smoothness independently of an observer's evaluation. A commonplace subjective measurement technique has been to measure the distinctness of image of a painted surface by observing the reflection of some standard pattern and assigning a figure of merit to the surface in accordance with the observer's judgment of the distinctness of the reflected image. It has previously been proposed to provide an instrument for measuring the distinctness of image independently of any subjective judgment. Such an instrument projects light through an aperture onto the test surface and a detector senses the light reflected from the surface. A rotating chopper blade is located in front of the detector and a lens focusses an image of the aperture onto the blade. The sharpness or distinctness of the image depends upon the reflective quality of the surface. The rate of change of the detector signal is a measure of the distinctness of image. This arrangement requires that the test surface be flat; otherwise any curvature would defocus the image and mask the effects of the surface quality on the image distinctness. For many inspection applications measurements must be made on curved as well as flat panels so that the previous instrument is not applicable.

It is therefore an object of this invention to provide a distinctness of image meter useful for measuring the reflective quality of a surface whether flat or slightly curved.

The invention is carried out by providing an instrument having a light source for projection onto a test surface, a detector for measuring the reflective light, an aperture element in the light path which is adjacent either the detector or the light source, a chopper element adjacent the other of the detector or the light source, a lens for focussing the reflected image of one element onto the other element, an arrangement for changing the light path distance between the two elements to facilitate focussing the image for test surfaces of different degrees of curvature, and a circuit responsive to the detector output for determining the rate of change of the detector signal when the image is focussed, the rate of change being a measure of the reflective quality of the surface. The invention further comprehends a chopper with a plurality of blades spaced at various distances from the source to bring about the above mentioned variation of the distance between the elements.

The above and other advantages will become apparent from the following description taken in conjunction with the accompanying drawings wherein like reference numerals refer to like parts and wherein:

FIG. 1 is an elevational view of a distinctness of image instrument including circuitry in block diagram form according to the invention, and FIG. 2 is a view of the instrument of FIG. 1 taken along lines 2—2 thereof.

FIG. 1 shows a test surface 10 comprising, for example, a panel to be examined for surface quality by a distinctness of image measurement. The measurement instrument 12 comprises a housing 14 having at one end three feet 16 spaced in tripod fashion for engaging the test surface 10 and positioning the instrument relative to the surface. The housing has an optical compartment 18 in the end nearest the test surface for housing the optical components of the instrument and an electronics compartment 20 at the opposite end of the housing for containing the electronic components of the instrument. The end of the housing nearest the test surface 10 includes a window 22 which allows the passage of light to and from the optical compartment 18.

As shown in FIGS. 1 and 2 the compartment 18 contains a light source 24 mounted on a support 25 attached to one of the side walls of the housing 14, the light source projecting a beam of light through the window 22 onto the test surface 10. An optoelectronic detector 26 is positioned in the compartment 18 to receive light which is reflected from the surface 10 and re-enters the compartment through the window 22. An aperture plate 30 in front of the detector contains a slit or aperture 32 for passing a small portion of the light reflected from the surface 10. Broken line 33 denotes the light path from the source 24 to the detector 26. A chopper 34 adjacent the light source 24 and a constant speed motor 36 for driving the chopper are mounted on a support 38 which is attached to another side wall of the housing 14. The chopper comprises a rotary disc 40 carrying eight axially extending blades 42a through 42h each mounted a different radial distance from the axis of rotation and each arranged to pass in front of the light source through the light beam. An imaging lens 44 is supported between the window 22 and the aperture plate 30 for focussing an image of a chopper blade 42 onto the aperture plate. As the edge of the blade image passes over the slit 32 the light passed to the detector is cut off and the detector output is reduced accordingly. If the chopper blade image is distinct, that is, focussed sharply on the plate, the light to the detector diminishes quickly and the detector signal changes at a fast rate. This indicates a high reflective quality of the test surface 10. Where the surface is relatively rough or diffused the chopper blade image cannot be sharply focussed on the aperture plate but rather is blurred. In that case the light to the detector decreases less quickly and the rate of change of the detector signal is relatively small. Thus the distinctness of image determines the rate of change of the edge of the blade image as it passes in front of the aperture so that the rate of change of the detector signal is useful as a measure of the distinctness of image.

If the test surface 10 is planar only one of the blades 42a through 42h can be focussed onto the aperture plate 30. When the surface 10 is not planar but has a curvature another one of the blades 42 will be focussed onto the aperture plate and the particular blade which is focussed will depend upon the degree of curvature. While there are not an infinite number of blades 42 to accommodate every possible degree of curvature, it has been found that as long as there is substantially good focus of the image then the measurement of the reflective quality of the surface can be made with acceptable accuracy. The provision of eight blades spaced from the light source at eight different distances allows substantially good focussing of a blade image over a large range of surface curvatures. A meter designed according to the configuration of FIG. 1 was suitable for flat surfaces and a range of convex surfaces having radii of curvature as small as 30 inches. The blade 42a farthest from the light source 24 is focussed on the aperture plate when flat surfaces are measured and the blades closer to the light source are focussed for various convex surfaces. When concave surfaces are to be tested the chopper design and the focal length of lens 44 must be selected to accommodate them. Since only one blade can be in substantial focus for a given surface the signal change produced by the image of that blade is the only one which should be used as a measure of the distinctness of image. That is accomplished by selecting of all the signal changes the one with the largest rate of change.

The circuitry for accomplishing this comprises an amplifier 50 coupled to the detector output for providing a signal to a sample and hold circuit 52 which stores several signal values during each signal rise, an analog-to-digital circuit 54 which digitizes the sampled values and passes them to the memory of a microcomputer 58 which is programmed to determine from the collected data the distinctness of image of the surface 10. A synch circuit 58 provides another input to the microcomputer 56 giving information on which chopper blade is in the light path. Since the blades are at different distances from the center of the rotary disc 40 they, as well as their images, move at different linear speeds. The measured signal rate of change must be adjusted, or normalized to make up for that speed difference. To identify the blade in the light path, a mirror 60 adjacent the blade 42a is positioned at an angle to the light beam to reflect the beam to a detector 62 on the housing wall when the blade 42a is blocking the light beam. The detector 62 sends a pulse to the synch circuit 58 which in turn sends a pulse to the microcomputer which is then able to identify the signal rise associated with the blade 42a and, by counting the signal rise, to identify and assign a normalization factor to each signal rise.

The microcomputer is programmed to (1) measure the time required for each signal rise to increase from 25% to 75% of its maximum value, (2) normalize the measured times by multiplying by a different factor for each chopper blade, (3) select the shortest measured time, and (4) look up in a table a distinctness of image value corresponding to the shortest time. The microcomputer output drives a display 64 showing the distinctness of image value.

It will thus be seen that according to this invention an instrument is provided for producing an objective measurement of the reflective quality of a surface such as the panel of a painted automobile even though the panel may be flat or curved.

The embodiments of the invention in which an exclusive property of privilege is claimed are defined as follows:

1. A distinctness of image instrument for measuring the reflective quality of a surface comprising:

a light source and a light detector defining an optical path therebetween, the detector providing an electrical output signal responsive to detected light, means for positioning the instrument relative to the surface to be measured such that light from the source is reflected by the surface to the detector, an aperture means in the optical path near one of the sources and the detector, a motor driven chopper having a plurality of blades near the other of the source and the detector, the chopper being driven at a constant speed for periodically interrupting the light path, lens means in the optical path for substantially focussing the image of one of the aperture means and a chopper blade on the other for a planar surface, the image being subject to defocussing when the surface is non-planar, the chopper blades being positioned at various spacings from the source to interrupt the light path at different axial positions along the path for varying the optical path length between the aperture means and the chopper blades for substantially focussing the image for at least one blade when the surface is non-planar, and an electrical circuit for determining the rate of change of the detector signal for each light interruption and selecting the maximum rate of change as a measure of the reflective quality of the surface.

2. A distinctness of image instrument for measuring the reflective quality of a surface comprising:

a light source and a light detector defining an optical path therebetween, the detector providing an electrical output signal responsive to detected light, means for positioning the instrument relative to the surface to be measured such that light from the source is reflected by the surface to the detector, an aperture plate defining an aperture in the optical path near the detector, a motor driven chopper near the source, the chopper having a plurality of blades positioned to pass through the light path at different distances from the source thereby varying the optical path length between the aperture plate and the various blades, the passage of each blade through the light path effecting a change in the detector signal, lens means in the optical path for substantially focussing the image of one of the chopper blades on the aperture plate, the image most nearly in focus depending on the curvature of the surface, and an electrical circuit for determining the rate of change of the detector signal for the image most nearly in focus, wherein the said rate of change is a measure of the reflective quality of the surface.

* * * * *